(12) United States Patent
Biedermann et al.

(10) Patent No.: US 8,486,121 B2
(45) Date of Patent: Jul. 16, 2013

(54) BONE ANCHORING DEVICE

(75) Inventors: Lutz Biedermann, VS-Villingen (DE); Wilfried Matthis, Weisweil (DE); Minh Q. Dinh, Fremont, CA (US); Scott Carpenter, Fremont, CA (US); Raghuveer Basude, Fremont, CA (US); Tracy Lopes, New Brunswick, NJ (US); Scott M. Russell, San Jose, CA (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/285,784

(22) Filed: Oct. 31, 2011

(65) Prior Publication Data

US 2012/0109223 A1 May 3, 2012

Related U.S. Application Data

(63) Continuation of application No. 11/646,973, filed on Dec. 27, 2006, now Pat. No. 8,080,044.

(60) Provisional application No. 60/776,609, filed on Feb. 23, 2006.

(30) Foreign Application Priority Data

Feb. 23, 2006 (EP) .................................. 06003733

(51) Int. Cl.
*A61B 17/04* (2006.01)
*A61B 17/86* (2006.01)
*A61F 2/08* (2006.01)

(52) U.S. Cl.
USPC .......................................... 606/313; 606/310

(58) Field of Classification Search
USPC ................................................... 606/300–321
See application file for complete search history.

(56) References Cited

U.S. PATENT DOCUMENTS

| 3,987,698 | A | * | 10/1976 | Rabe ............................. 411/455 |
| 4,331,423 | A | | 5/1982 | Yanney, Jr. |
| 4,776,328 | A | | 10/1988 | Frey et al. |
| 5,209,753 | A | | 5/1993 | Biedermann et al. |
| 5,380,334 | A | * | 1/1995 | Torrie et al. ................... 606/104 |
| 5,562,704 | A | | 10/1996 | Tamminmäki et al. |
| 5,601,558 | A | | 2/1997 | Torrie et al. |
| 5,662,654 | A | | 9/1997 | Thompson |
| 5,735,898 | A | | 4/1998 | Brånemark |

(Continued)

FOREIGN PATENT DOCUMENTS

| DE | 10 2004 009 429 A1 | 9/2005 |
| JP | 2005-237965 A | 9/2005 |

OTHER PUBLICATIONS

European Search Report for European Application No. 06003733.0-2318 dated Jun. 28, 2006 and mailed Jul. 5, 2006, 6 pp.

*Primary Examiner* — Sameh Boles
(74) *Attorney, Agent, or Firm* — Christie, Parker & Hale, LLP (57) ABSTRACT

A bone anchoring device includes a shaft for anchoring in a bone and a head, the shaft including a first section having a plurality of barb elements, the barb elements being elastically deformable relative to the body of the shaft, and a second section including a bone thread for engagement with the bone. The first section is located near the tip of the shaft and allows insertion by pushing whereas the second section provides enhanced resistance against pull-out.

17 Claims, 5 Drawing Sheets

U.S. PATENT DOCUMENTS

| | | |
|---|---|---|
| 5,849,004 A | 12/1998 | Bramlet |
| 6,428,317 B1 | 8/2002 | Abel |
| 6,447,513 B1 | 9/2002 | Griggs |
| 6,843,791 B2 | 1/2005 | Serhan |
| 2001/0000186 A1 | 4/2001 | Bramlet et al. |
| 2003/0045885 A1 | 3/2003 | Margulies et al. |
| 2004/0122431 A1 | 6/2004 | Biedermann et al. |
| 2005/0159749 A1 | 7/2005 | Levy et al. |
| 2005/0165395 A1 | 7/2005 | Orbay et al. |
| 2005/0187555 A1* | 8/2005 | Biedermann et al. ........... 606/72 |
| 2006/0264952 A1 | 11/2006 | Nelson et al. |

* cited by examiner

BONE ANCHORING DEVICE

CROSS-REFERENCE TO RELATED APPLICATION(S)

This application is a continuation of allowed U.S. patent application Ser. No. 11/646,973, filed Dec. 27, 2006 now U.S. Pat. No. 8,080,044, which claims the benefit of U.S. Provisional Patent Application Ser. No. 60/776,609, filed Feb. 23, 2006, and claims priority from European Patent Application 06003733.0, filed Feb. 23, 2006, the entire disclosures of which are incorporated herein by reference.

BACKGROUND

The present invention relates to a bone anchoring device. In particular, it relates to a bone anchoring device which comprises a first section with elastically deformable barb elements for push and turn insertion and an additional second section with a bone thread for enhanced retention in the bone. The bone anchoring device can be used for example in the form of a pedicle screw for the application in spinal surgery or in any other type of bone anchor application.

A known form of a bone anchoring element is a conventional bone screw comprising a shaft with a bone thread for screwing the screw into a bone. The bone screw is manually inserted into the bone by means of a screw driver, which is a time-consuming and force-requiring process. Moreover, during the process in which the screw is inserted into the bone, high pressure forces may be acting on the bone structure itself, which is undesirable in certain clinical applications such as e.g., in neuro surgery, spinal surgery, pediatric surgery or trauma surgery.

U.S. Pat. No. 5,562,704 discloses a surgical implant having a body with a first end formed as a stem and a second end formed as a head. The implant comprises a plurality of cuts defining barbs which are intended to keep the implant installed in the position of use.

US 2005/0187555 A1 discloses a bone anchoring element comprising a shaft with a plurality of elastically deformable barb elements which are arranged in at least one helical line around the shaft. The design of the bone anchoring device allows a fast and easy insertion into the bone. Therefore, it is a so-called push and turn anchor. However, the pull-out force may be reduced depending on the bone quality compared to conventional bone screws. In one embodiment the bone anchoring device comprises a first section having the barb elements which is located near the tip, and adjacent to the first section, a second section having a metric thread onto which an outer nut can be screwed to fix a bone plate to the bone.

Based on the foregoing, there is a need to provide a bone anchoring device which can be inserted by pushing it into the bone and which at the same time offers increased resistance against pull-out and rotational forces.

SUMMARY

The bone anchoring device according to the invention combines the features of both, the conventional screws and the push and turn anchors. It can be used as a pedicle anchor which is anchored with the elastically deformable barb elements in the weaker inner vertebral body having a bone structure of cancellous bone and with the conventional screw portion within the stronger pedicle region of cortical bone. However, the bone anchoring device can be applied in any similar bone anchoring situation in which the bone has a weaker region and adjacent thereto a harder region.

Due to the portion having a bone thread, the bone anchoring device provides the familiar screw feeling and anchoring assurance to the surgeon.

The bone anchoring device resists against pull-out and rotational forces compared to the known push and turn anchor, especially with weak bone substance. It provides a low insertion force and a high restraining force. In addition, it provides a low torque insertion and removal of the anchoring device.

With the anchoring device according to the invention the time for the insertion procedure and possible removal procedure is improved due to the push and turn insertion and, if required, a safe removal later on.

Furthermore, the anchoring device provides fine-tuning of the bone anchor seating height in comparison to push and turn anchors.

The anchoring device can be partly or fully made of a super-elastic and/or shape-memory material. In particular the barb elements can have super-elastic or shape-memory features.

BRIEF DESCRIPTION OF THE DRAWINGS

Further features of the invention will become apparent and will be best understood by reference to the following detailed description of embodiments taken in conjunction with the accompanying drawings.

DETAILED DESCRIPTION OF THE INVENTION

A bone anchoring device according to a first embodiment of the invention is described with reference to FIGS. 1 to 4. The bone anchoring device 1 comprises a shaft 2 with a tip 3 at one end and a head 4 at the other end. The shaft 2 comprises a first section 5 with a plurality of barb elements 6 and a second section 7 comprising a bone thread. The first section 5 is located between the second section 7 and the tip 3. The second section 7 which has the bone thread is located adjacent to or in the vicinity of the head 4 of the anchoring device.

Figures 1, 2, 3, 4:
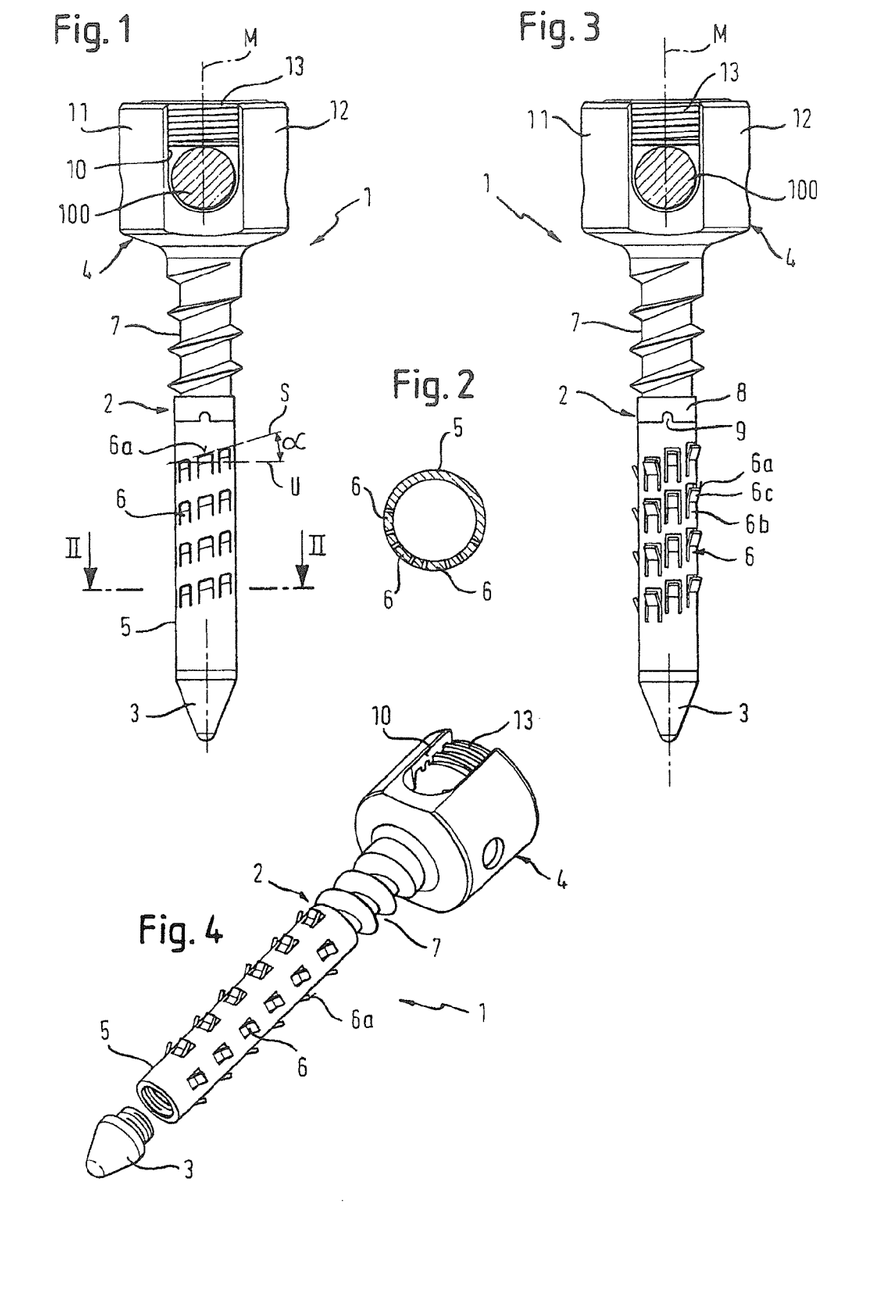
FIG. 1 shows a side view of a bone anchoring device according to a first embodiment in a first condition.
FIG. 2 shows a cross-sectional view of the bone anchoring device of FIG. 1 along a line A-A.
FIG. 3 shows the bone anchoring device of FIG. 1 in a second condition with expanded barb elements.
FIG. 4 shows a partially exploded view of the bone anchoring device of FIG. 3.

The first section 5 is preferably formed as a tubular body, as shown in FIG. 4. The barb elements 6 are formed by substantially quadrangular cuts made in the wall of the tubular body, wherein the end base of each barb element 6 is not cut out from the tubular body and acts as the attachment and a bending side for the barb elements 6 in the wall of the tubular body. The arrangement of the barb elements 6 is such that the free ends 6a of the barb elements face away from the tip 3.

Further, as can be seen best in FIG. 1, the barb elements 6 are arranged such that their free ends 6a lie substantially on a helical line S around the shaft axis M. Hence, the free ends 6a of the barb elements are inclined by an angle α with regard to the circular circumference line U, the angle α corresponding to the helical angle of the helical line S. Therefore, the free ends 6a of the barb element form cutting edges similar to the crests of a screw thread. For providing an appropriate screw-like characteristic, the barb elements form at least one full turn of the helix, and preferably, at least two turns of the helix.

The barb elements 6 project from the surface of the tubular body at an angle which is selected during the manufacturing process based on the material used and the actual dimensions of the barb elements 6 so that a desired stiffness of the barb elements is obtained. Due to their configuration and attachment to the wall of the tubular body, the barb elements 6 are elastically deformable relative to the tubular body. When the barb elements 6 are collapsed or pressed into the cuts, they are pre-tensioned.

Preferably, the barb elements 6 have a first section 6b which is approximately parallel to the wall and a second section 6c which is inclined outwards.

FIG. 1 shows a first condition in which the barb elements 6 are lying completely or nearly completely within the respective cuts in the wall of the tubular body. Hence, in the first condition, the barb elements 6 do not project from the shaft 2. FIG. 3 shows a second condition, where the barb elements 6 project outward from the shaft 2.

The number of the barb elements 6 can vary. The retention force generated by the barb elements 6 in the bone is dependent on the number of barb elements 6 and increases with the number of barb elements 6.

The pitch of the helical line S provided by the cutting edges 6a of the barb elements 6 is the same as the pitch of the bone thread provided at the second section 7. This allows screwing the anchoring device 1 in the bone and un-screwing it from the bone, if necessary. As can be seen in FIG. 3 the outer diameter the first section 5, when the barb elements 6 are projecting outwards corresponds approximately to the outer diameter of the first section 7 having the bone thread. The length of the first section 5 is approximately twice the length of the second section 7 or more.

Preferably, the length of the threaded portion of the first section 7 is selected at least as large as the region of the bone having a compact bone structure.

The first section 7 can have a cylindrical section 8 free of bone thread to which the tubular body can be attached. To prevent rotation of the tubular body with respect to the second section 7, structures can be provided for example, one or more recesses 9 into which corresponding projections of the tubular body engage. However, many other possibilities of fixing the first section 5 to the second section 7 exist, for example screwing or press fitting, welding or other types of connections. Another manufacturing option is to have a one piece screw shaft which has already the threaded portion and a cylindrical portion which is a tube with barb elements. This may be connected together with a tip, for example with a threaded tip.

The tip 3 can be connected to the tubular body by means of screwing, press fitting, welding or any other type of connection.

The head 4 comprises on its side opposite to the tip 3 a recess 10 which is U-shaped or approximately U-shaped, by means of which two free legs 11,12 are formed defining a channel for receiving a rod 100. An internal thread is provided at the legs 11,12 for receiving an inner screw 13 for fixation of the rod 100 in the channel.

The bone anchoring device 1 can be made of any body-compatible material. Preferably, a body-compatible metal, such as titanium, stainless steel and their alloys, or a body-compatible plastic material can be used. The tubular body having the barb elements 6 can be made of the same material as that of the remainder of the anchoring device 1 or of a different material.

Preferably, the tubular body with the barb elements 6 is made of a shape-memory alloy having shape-memory and/or super-elastic characteristics or is made of a material having spring like characteristics like stainless steel or titanium alloys. For example, nickel titanium alloys such as nitinol are suitable for use for the tubular body.

In operation, the bone anchoring device 1 is initially pre-assembled by connecting the first section 5 consisting of the tubular body to the second section 7 and thereafter connecting the tip 3 to the tubular body.

Figure 5:
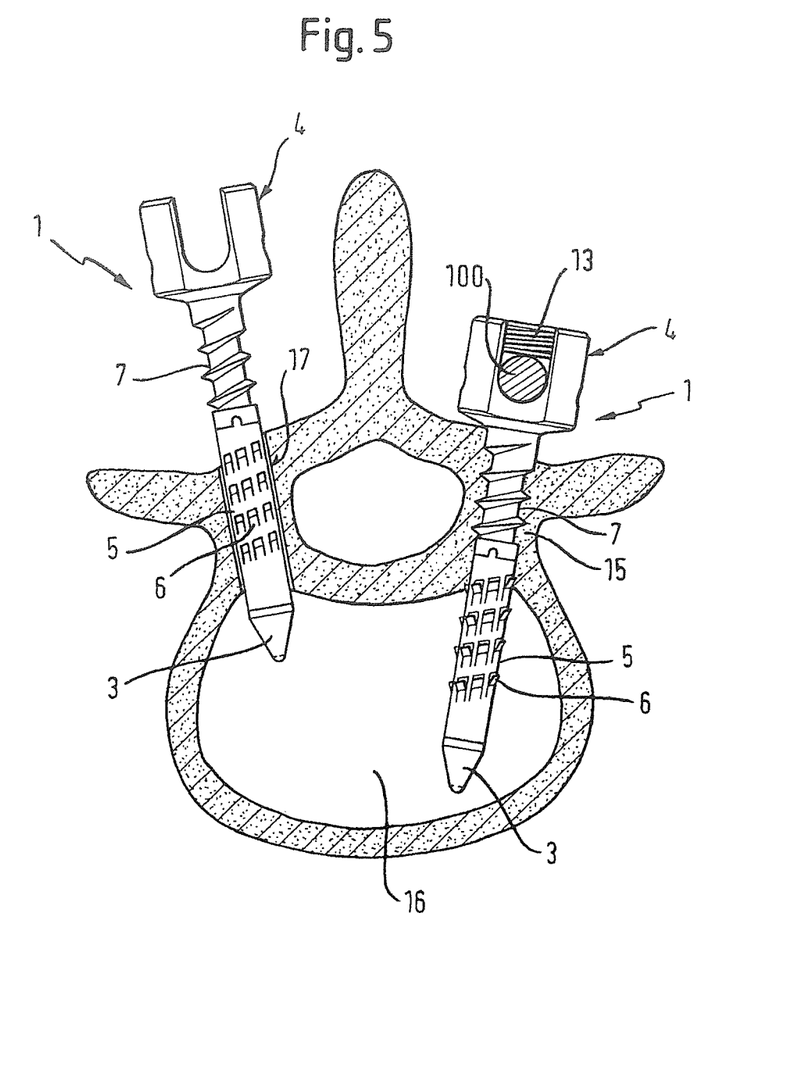
FIG. 5 shows the anchoring device according to the first embodiment in the process of being anchored in a vertebra.

FIG. 5 shows the use of the bone anchoring device in a vertebra. The inner vertebral body 16 consists of cancellous bone whereas the pedicle region 15 consists of cortical bone. First, a core hole 17 is prepared. The diameter of the core hole 17 corresponds essentially to the outer diameter of the tubular body or can be slightly larger or smaller depending on the desired result or the circumstances. For example, the diameter of the core hole 17 is selected depending on the diameter of the tubular body and the flexibility of the barb elements 6 so that a desired resistance to pull out is provided by the barb elements 6. The selected diameter depends also upon the bone quality.

Subsequently, as shown in the left side of FIG. 5 the bone anchoring device 1 is inserted by pushing it into the core hole 17. During insertion, the barb elements 6 are in a collapsed state and are pressed against or into the cuts due to their elasticity. The sliding motion enables the bone anchoring device 1 to be inserted rapidly and in a smooth way until the second section 7 with the bone thread comes into contact with the core hole 17.

As shown in the right side of FIG. 5, the bone anchoring device 1 is further screwed in with the bone thread engaging the surrounding bone material of the pedicle region. When inserted, the pre-tensioned barb elements 6 expand and rise up and press with their cutting edges 6a against the wall of the core hole 17.

For further and/or final positioning of the bone anchoring device in the core hole 17 or for positioning of the head 4 the bone anchoring device 1 is screwed further into the core hole 17 or screwed out therefrom like a screw. During the process, the edges 6a of the barb elements 6, being positioned on a helical line S, act like a thread. At least two bone anchoring devices 1 are inserted on one side of adjacent vertebrae, respectively, and connected via the rod 100.

Since the first section 5 of the anchoring device having the barb elements 6 is positioned near the tip 3 the first section enters into the weak bone material of the inner vertebral body without causing damage.

The second section 7 comprising the bone thread is placed in the compact cortical bone and, therefore, provides for a maximum restraining force to resist pull-out and rotation.

The bone anchoring device can be removed just like a bone screw by turning it in a counter-clockwise direction.

In a modification of operation, the tubular body including the barb elements is made of a material with shape-memory characteristics. The tubular body can be treated before the assembly of the bone anchoring device in such a way that the barb elements project at a body temperature or at an elevated temperature and are in a collapsed position at a lower temperature, e.g. at room temperature. In operation, the bone anchoring element with collapsed barb elements is pressed into the core hole. After warming up and equilibration to the body temperature or after heating by external application of heat by any other means the barb elements expand to their final position.

Figures 6, 7:
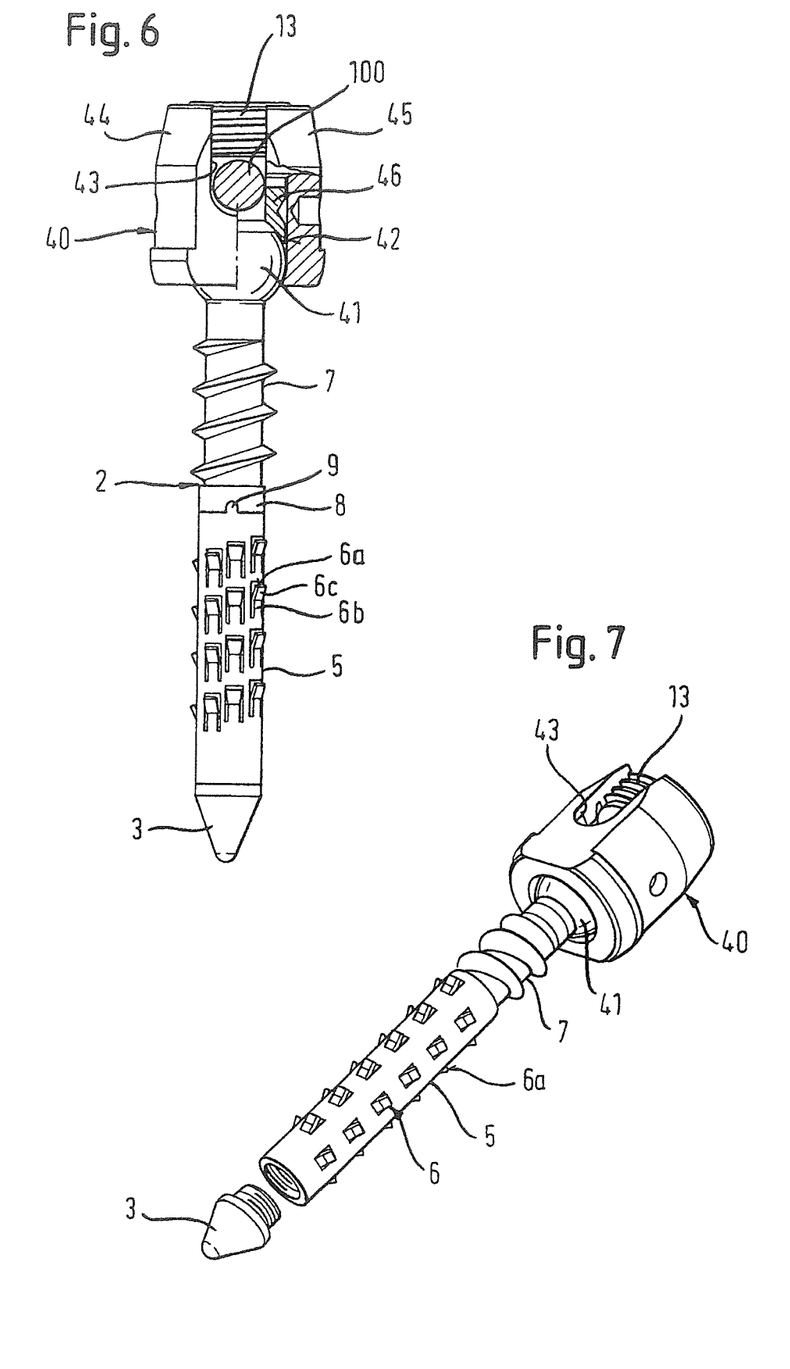
FIG. 6 shows a partially sectional side view of a bone anchoring device according to a second embodiment in the second condition corresponding to the first embodiment shown in FIG. 3.
FIG. 7 is a partially exploded view of the bone anchoring device of FIG. 6.

FIGS. 6 and 7 show a second embodiment which differs from the first embodiment only in the design of the head. Parts which are identical to the first embodiment have the same reference numbers and the description thereof shall not be repeated.

The bone anchoring device according to the second embodiment has a head 40 which is pivotably connected to the shaft 2. The shaft 2 comprises at its end opposite to the tip 3 a ball-shaped section 41. The head 40 comprises a coaxial bore 42 tapering towards one end to provide a seat for receiving the ball-shaped section 41 of the shaft. At the opposite end the head 40 comprises a U-shaped or approximately U-shaped recess 43 by means of which two legs 44,45 are formed defining a channel to receive the rod 100. An internal thread is provided at the legs to receive an inner screw 13 like in the first embodiment.

A pressure element 46 is provided by means of which pressure is exerted onto the ball-shaped section 41 to press the ball-shaped section 41 against the seat. If the inner screw 13 is not yet tightened, the shaft 2 can pivot with respect to the head 40.

The use of the bone anchoring device is similar to that of the first embodiment except that the head 40 can be rotated and pivoted relative to the shaft 2 to adjust its orientation with respect to the rod 100 so that the rod can be inserted in the channel. After inserting at least two bone anchoring devices into adjacent vertebrae, the rod 100 is inserted and fixed by the inner screw 13, thereby pressing via the pressure element 46 onto the ball-shaped section to lock the position of the head 40 relative to the shaft.

Figure 8:
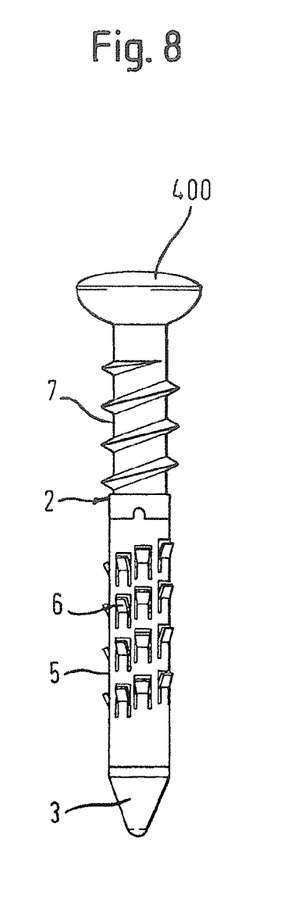
FIG. 8 shows a bone anchoring device according to a third embodiment.

FIG. 8 shows a third embodiment of the bone anchoring device. It differs from the previous embodiments only in that the head 400 is shaped as the head of a conventional bone screw. For example, it has a lens shape, but any other shape of the head can be selected. The head 400 preferably has means (not shown) for engagement with a screwing-in tool, such as for example a hexagon recess. Furthermore, the head 400 can be formed integrally with the shaft 2 or with a part of the shaft. The bone anchoring device according to this embodiment can be used, for example, to fix a plate to the bone.

Figure 9:
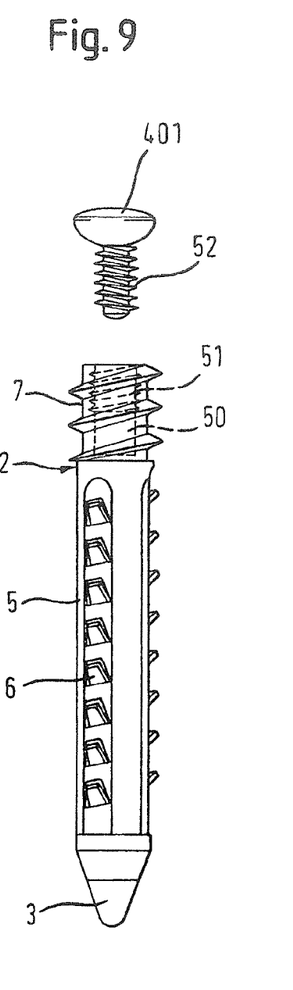
FIG. 9 shows a partially exploded view of a bone anchoring device according to a fourth embodiment.

FIG. 9 shows a fourth embodiment of the bone anchoring device which differs from the previous embodiments mainly in the design of the head portion. The shaft 2 has at the end which is opposite to the tip 3 a coaxial bore 50 with an internal thread 51. The head 401 is formed as a separate part. It has a projection 52 with an external thread so that it can be screwed-in into the bore 50 to connect the head 401 and the shaft 2. However, the connection between the head 401 and the shaft 2 is not limited to a screw connection. It can be any other detachable connection. The barb elements 6 shown in connection with this embodiment are provided on plates which are attached to the shaft body. In this case, the shaft body can be a full cylinder. However, it is also possible that the shaft is formed like that of the previous embodiments.

Figure 10:
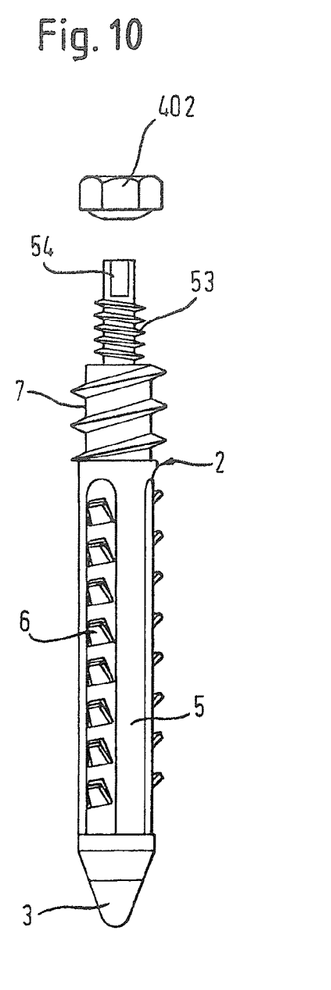
FIG. 10 shows a partially exploded view of a bone anchoring device according to a fifth embodiment.

FIG. 10 shows a fifth embodiment of the bone anchoring device which differs from the previous embodiments only in the design of the head portion. The shaft has at the end which is opposite to the tip 3 a projection 53 with an external thread which is a metric thread or another thread except a bone thread. A nut member 402 is provided which cooperates with the thread on the projection. Preferably, the projection has a recess 54 for engagement with a screwing-in tool. The bone anchoring device can be used with a bone plate.

Figure 11:
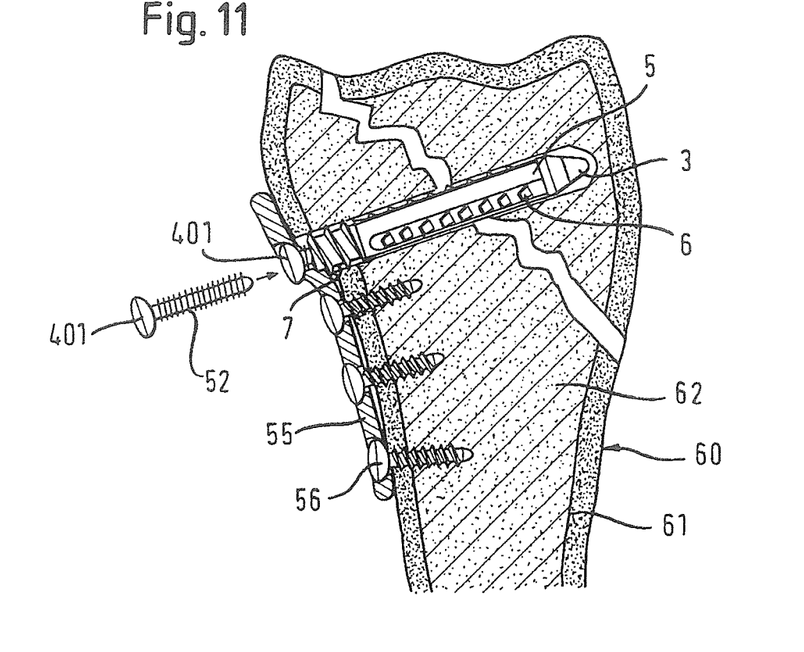
FIG. 11 is a schematic representation of the bone anchoring device of FIG. 9 as applied to a fracture of the tibia.

FIG. 11 shows the application of the bone anchoring device of FIG. 9 together with a bone plate 55 and conventional bone screws 56 in the fixation of a fracture of the tibia 60. First, the bone anchoring device is pushed into the core hole and at the end of the insertion process screwed-in while the head 401 is still separated. The screwing can be carried out by means of a tool cooperation with the internal thread 51.

Then, the bone plate 55 is applied and fixed with conventional bone screws 56. Finally, the head 401 is connected to the bone anchoring device thereby pressing onto the plate 55 for final fixation. As can be seen in the figure, the length of the second section of the shaft which has the bone thread is equal or slightly larger than the depth of the bone region 61 which consists of a compact structure whereas the section of the shaft having the barb elements 6 is substantially larger and engages the region 62 of the bone which consists of the weaker bone material.

Figure 12:
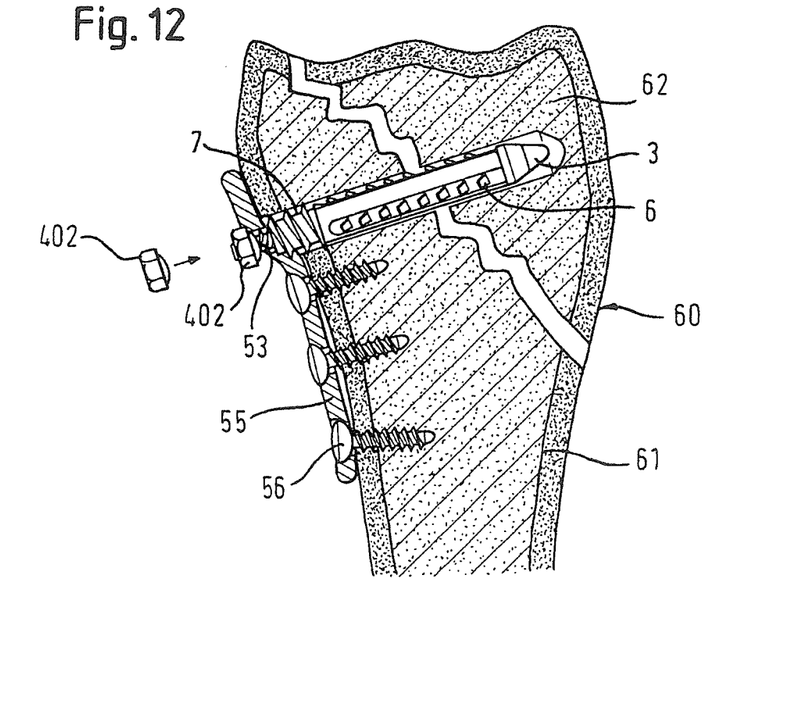
FIG. 12 is a schematic representation of the bone anchoring device of FIG. 10 as applied to a fracture of a tibia.

FIG. 12 shows in a similar manner the application of the bone anchoring device of FIG. 10 in the fixation of a broken tibia. Instead of connecting the head with the shaft, the nut member 402 is screwed onto the projection 53.

Modifications of the embodiments are possible. The barb elements 6 can have another shape, for example, they can have a trapezoidal shape. The barb elements 6 can be shaped without the inclined section shown in FIGS. 3 and 6. The barb elements may not need to be provided over the whole length between the second section 7 having the bone thread, and the tip 3. For example, two turns of a helix provided by the barb elements 6 can be sufficient.

The first section 5 having the barb elements 6 does not need to have the shape of a tubular body but can be, for example, a full cylinder. The barb elements 6 are then cut into the wall or otherwise provided at the wall, if a material is selected which allows manufacturing in this way.

The first section 5 and the second section 7 can be formed integrally. Also, the tip 3 can be formed integrally with the shaft 2.

The bone thread and the helix generated by the barb elements 6 can have the shape of a single helix or a double or multiple helix. In particular, the bone thread can be a single or a multiple bone thread.

The polyaxial bone anchoring device according to the second embodiment has a different head. Many types of polyaxial screws are known and can be used in connection with the shaft. For example, a concept is known according to which it is possible to independently lock the ball-shaped head and the rod in its position, respectively.

The head can be any structure which is suitable for connection with an separate device such as, for example, a rod or a plate. The head can also be a specific end portion of the shaft in the vicinity of the bone thread section.

The invention is not limited to the embodiments described above which show a pedicle anchor which is to be connected with a rod used in spinal surgery and a bone anchor which is to be connected with a plate used in trauma surgery. It can be used in other orthopedic applications where bone anchors are required.

What is claimed is:

1. A bone anchoring device comprising:
   a head portion; and
   a shaft for anchoring in a bone, the shaft comprising:
   a first section comprising a plurality of barb elements, the barb elements being elastically deformable relative to the shaft, and
   a second section comprising a bone thread for engagement with the bone;
   wherein the shaft has a free end opposite to the head portion and the first section is provided between the second section and the free end;
   wherein the barb elements are arranged on at least one helical line around the shaft; and
   wherein a pitch of the helical line is the same as a pitch of the bone thread of the second section.

2. The bone anchoring device of claim 1, wherein the second section is arranged adjacent to the head portion.

3. The bone anchoring device of claim 1, wherein the barb elements form at least two turns of the helical line.

4. The bone anchoring device of claim 1, wherein the first section is detachably mounted to the second section.

5. The bone anchoring device of claim 1, wherein the first section is provided on a tubular body.

6. The bone anchoring device of claim 5, wherein the barb elements are cut out of a wall of the tubular body.

7. The bone anchoring device of claim 1, wherein the head portion comprises a recess for receiving a rod.

8. The bone anchoring device of claim 1, wherein the head and the shaft are fixedly connected.

9. The bone anchoring device of claim 1, wherein the head and the shaft are connected such as to allow pivoting of the shaft relative to the head.

10. The bone anchoring device of claim 9, comprising means for locking the pivoting movement of the shaft relative to the head.

11. The bone anchoring device of claim 1, wherein the barb elements are made of a shape-memory material.

12. The bone anchoring device of claim 11, wherein the barb elements comprise nitinol.

13. The bone anchoring device of claim 1, wherein free ends of the barb elements face towards the head portion.

14. The bone anchoring device of claim 1, wherein the barb elements are arranged to prevent extraction without rotation of the bone anchoring device.

15. The bone anchoring device of claim 1, wherein the head and the shaft are separate parts.

16. A bone anchoring device comprising:
    a head portion; and
    a shaft for anchoring in a bone, the shaft comprising:
    a first section comprising a plurality of barb elements, the barb elements being elastically deformable relative to the shaft, and
    a second section comprising a bone thread for engagement with the bone;
    wherein the shaft has a free end opposite to the head portion and the first section is provided between the second section and the free end, and
    wherein the length of the first section is at least approximately twice the length of the second section.

17. A bone anchoring comprising:
    a head portion; and
    a shaft for anchoring in a bone, the shaft comprising:
    a first section comprising a plurality of barb elements arranged on at least one helical line around the shaft, the barb elements being elastically deformable relative to the shaft; and
    a second section comprising a bone thread for engagement with the bone; and
    wherein a pitch of the helical line is the same as a pitch of the bone thread of the second section.

* * * * *